US008263106B2

(12) United States Patent
Park et al.

(10) Patent No.: US 8,263,106 B2
(45) Date of Patent: Sep. 11, 2012

(54) GOLD-COATED STENT, OLIGONUCLEOTIDE BOUND GOLD-COATED STENT, AND PROCESS FOR PRODUCING THE SAME

(75) Inventors: Han-Oh Park, Daejeon (KR); Jae-Don Lee, Daejeon (KR); Sam-Yong Lee, Daejeon (KR); Eun-Jung Jung, Daegu (KR)

(73) Assignee: Bioneer Corporation, Daejeon (KR)

( * ) Notice: Subject to any disclaimer, the term of this patent is extended or adjusted under 35 U.S.C. 154(b) by 80 days.

(21) Appl. No.: 12/665,404

(22) PCT Filed: Jun. 16, 2008

(86) PCT No.: PCT/KR2008/003385
§ 371 (c)(1),
(2), (4) Date: Jun. 11, 2010

(87) PCT Pub. No.: WO2008/156270
PCT Pub. Date: Dec. 24, 2008

(65) Prior Publication Data
US 2010/0255055 A1   Oct. 7, 2010

(30) Foreign Application Priority Data
Jun. 19, 2007  (KR) ........................ 10-2007-0059828

(51) Int. Cl.
*A61F 2/00*  (2006.01)
*A61F 2/02*  (2006.01)
*A61F 2/04*  (2006.01)
*A61F 2/06*  (2006.01)

(52) U.S. Cl. ...................... 424/423; 623/1.15; 623/23.7
(58) Field of Classification Search .................... None
See application file for complete search history.

(56) References Cited

U.S. PATENT DOCUMENTS

| 5,464,650 | A | 11/1995 | Berg et al. |
| 6,398,806 | B1 | 6/2002 | You |
| 6,712,846 | B1 | 3/2004 | Kraus et al. |
| 6,767,944 | B2 | 7/2004 | Zobel et al. |
| 2004/0063654 | A1 | 4/2004 | Davis et al. |
| 2006/0073336 | A1* | 4/2006 | Zhang et al. ................ 428/407 |

OTHER PUBLICATIONS

Tombelli et al. "Improved Procedures for Immobilisation of Oligonucleotides on Gold-Coated Piezoelectric Quartz Crystals", Biosensors and Bioelectronics; 17 (2002), pp. 929-936.*

* cited by examiner

*Primary Examiner* — Bethany Barham
*Assistant Examiner* — Jeffrey T Palenik
(74) *Attorney, Agent, or Firm* — Clark & Brody

(57) ABSTRACT

The present invention relates to a gold-plated stent and its preparation method. More specifically, it relates to a gold-plated stent that is coated with various chemical materials such as 2-aminoalkanethiol, epihalogenhydrin, and diamine compounds in a sequence and also oligonucleotide gold-plated stent, which is prepared by binding oligonucleotide, a biomaterial, to the gold-plated stent coated with said chemicals. The oligonucleotide gold-plated stent of the present invention has an advantages of raising the local concentration in injured parts and minimizing the toxicity overall the body, so it can be used for prevention of restenosis after angioplasty.

10 Claims, 13 Drawing Sheets

[Fig. 1]
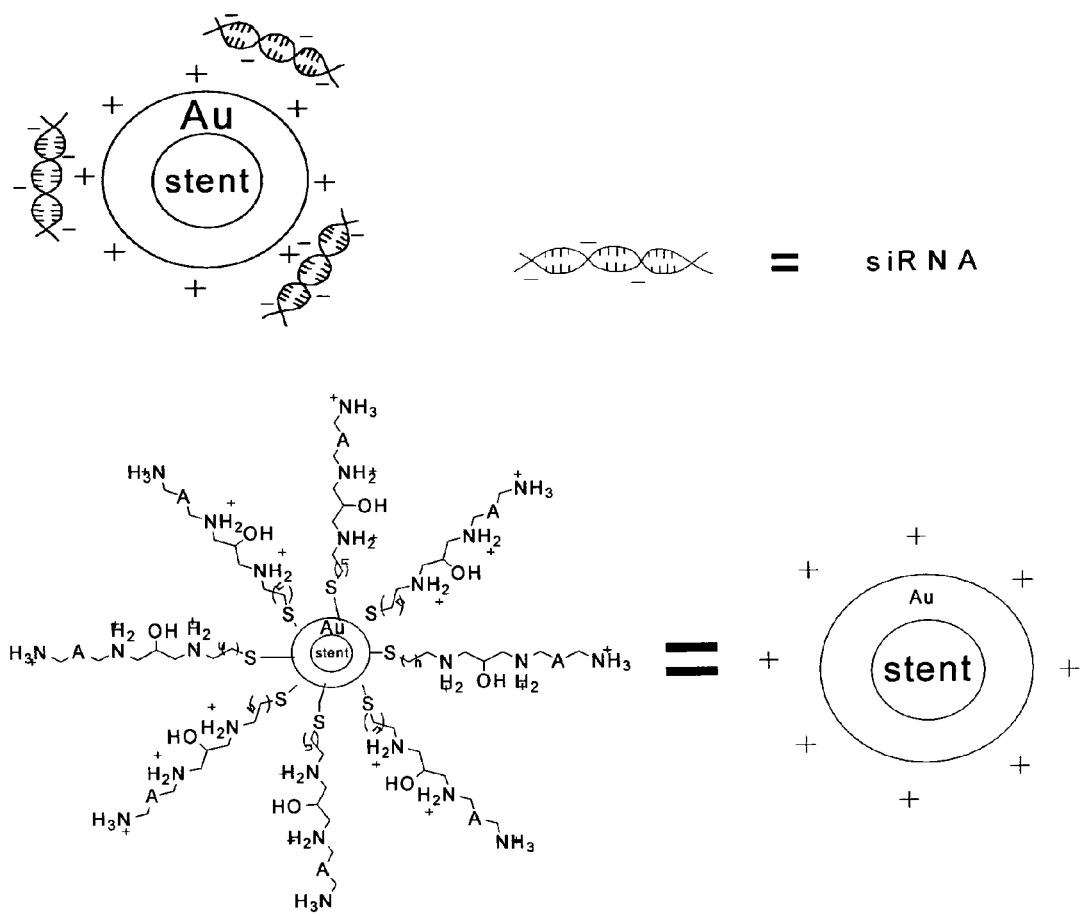

[Fig. 2]
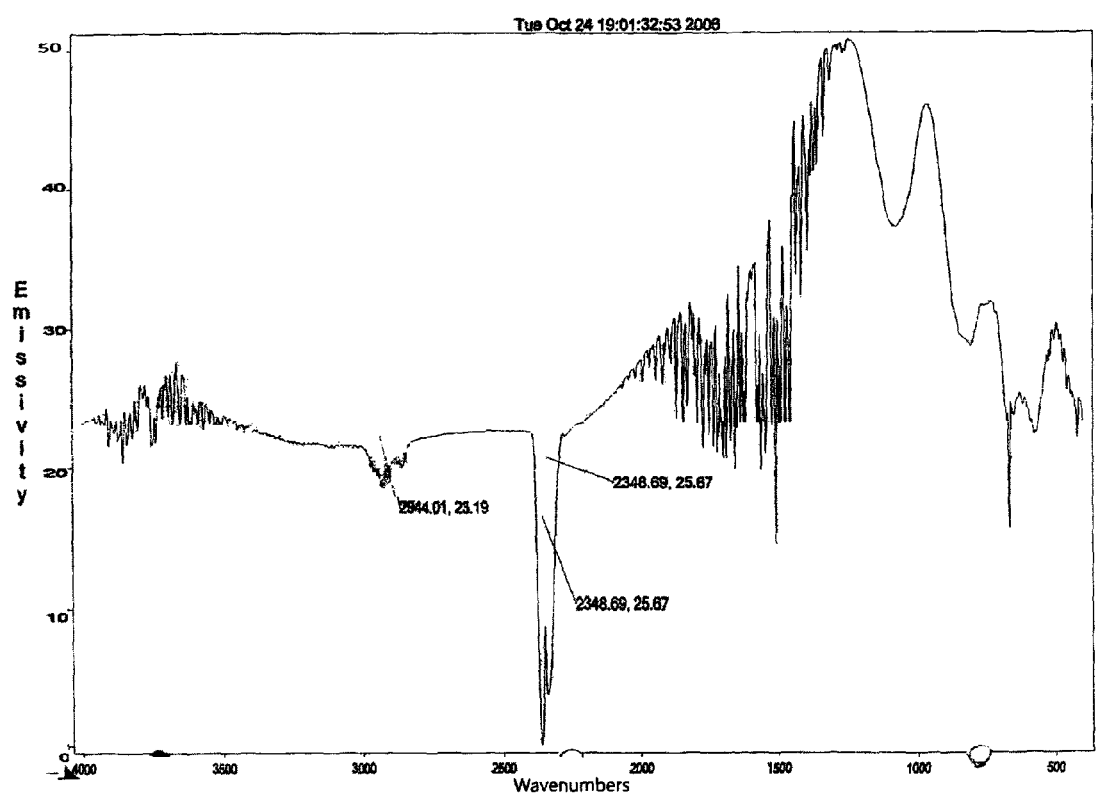

[Fig. 3]
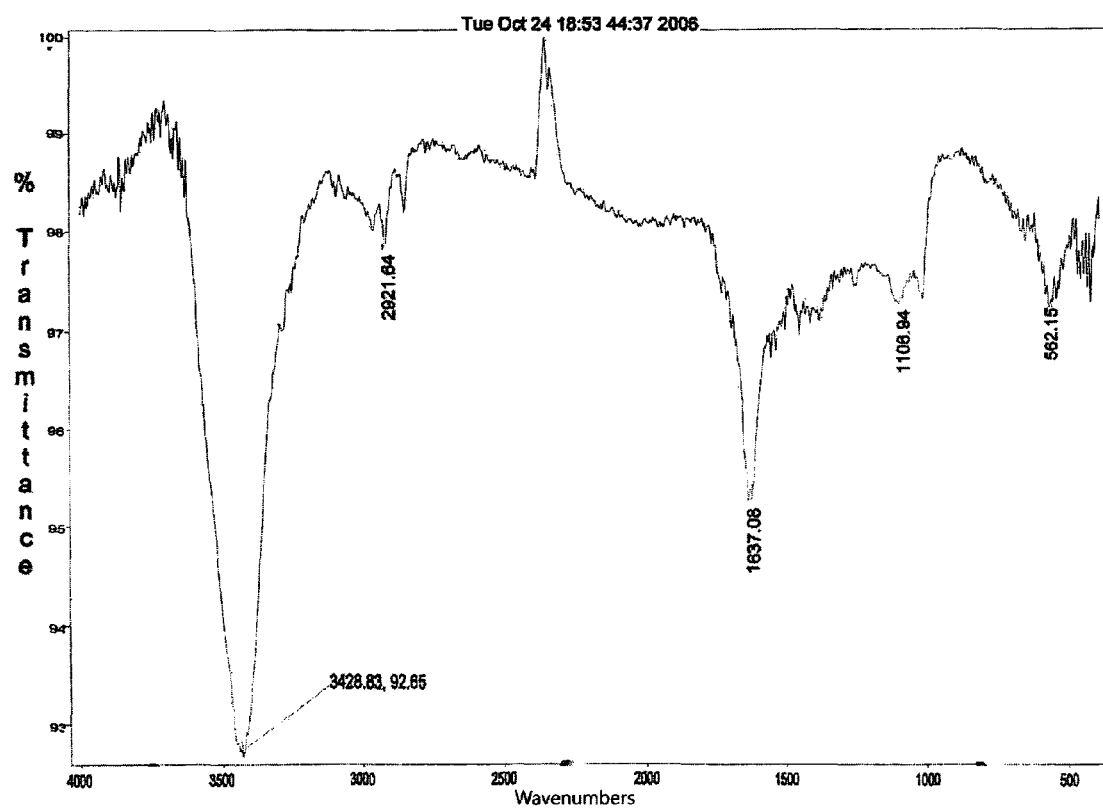

[Fig. 4]
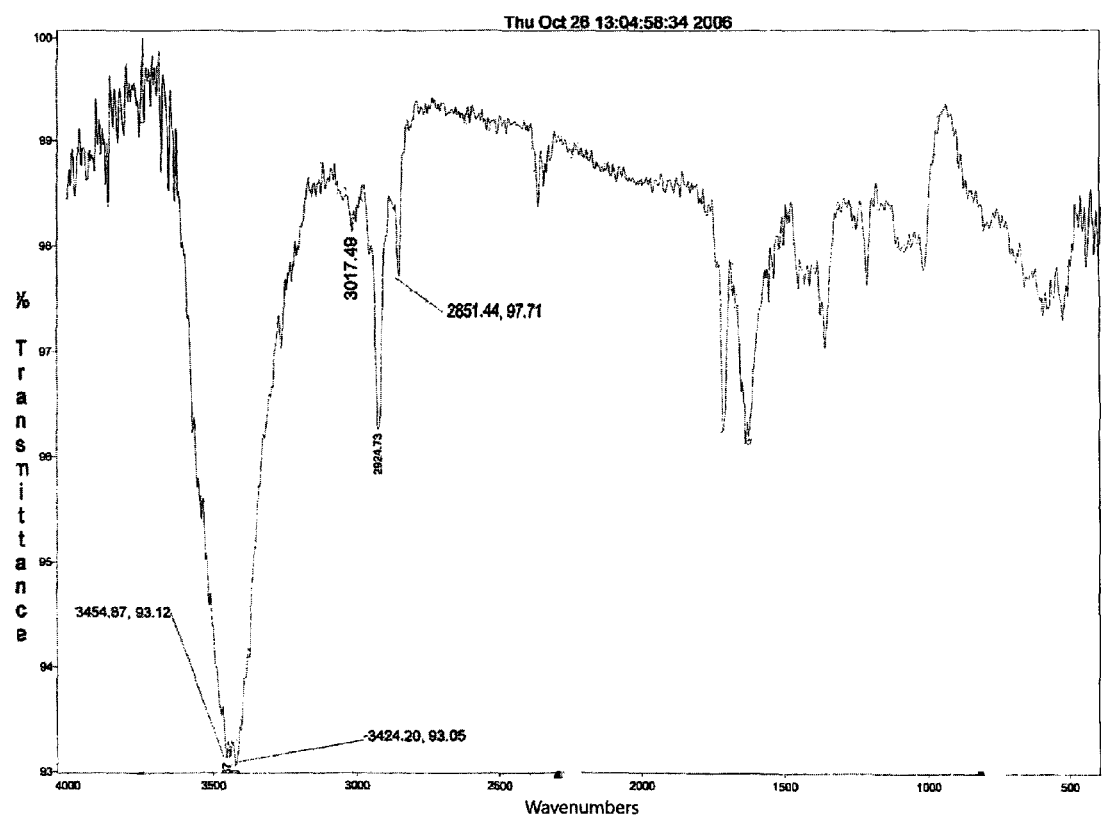

[Fig. 5]
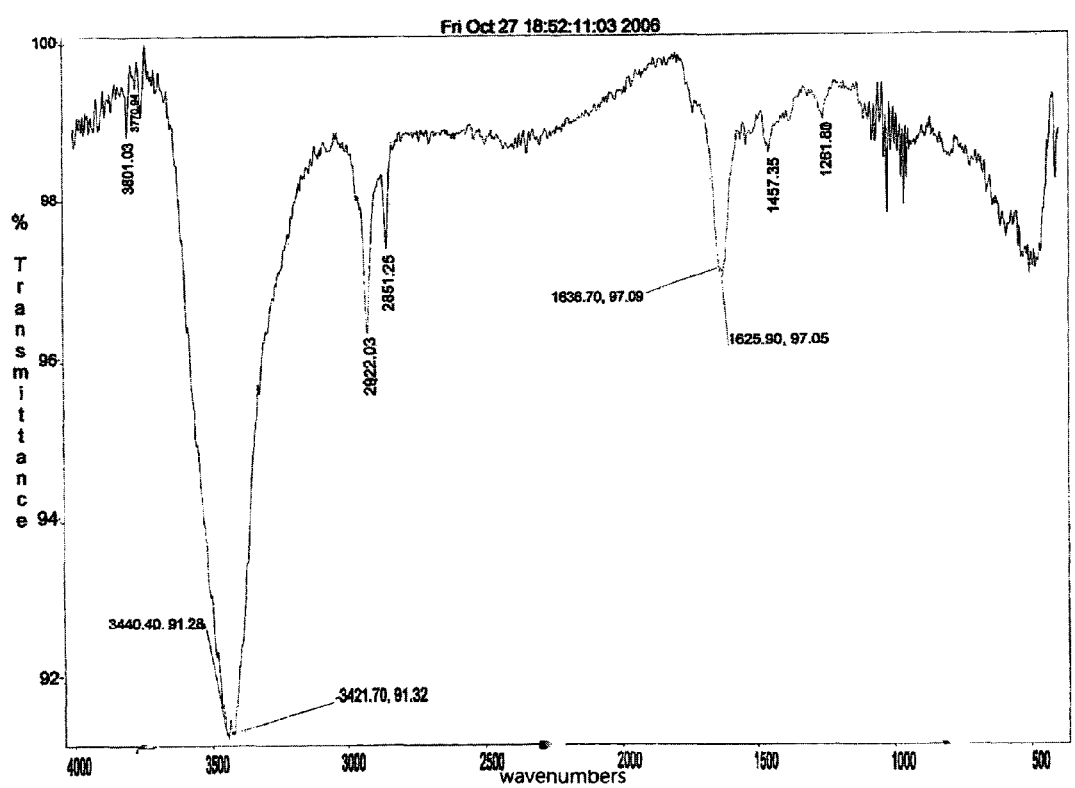

[Fig. 6]
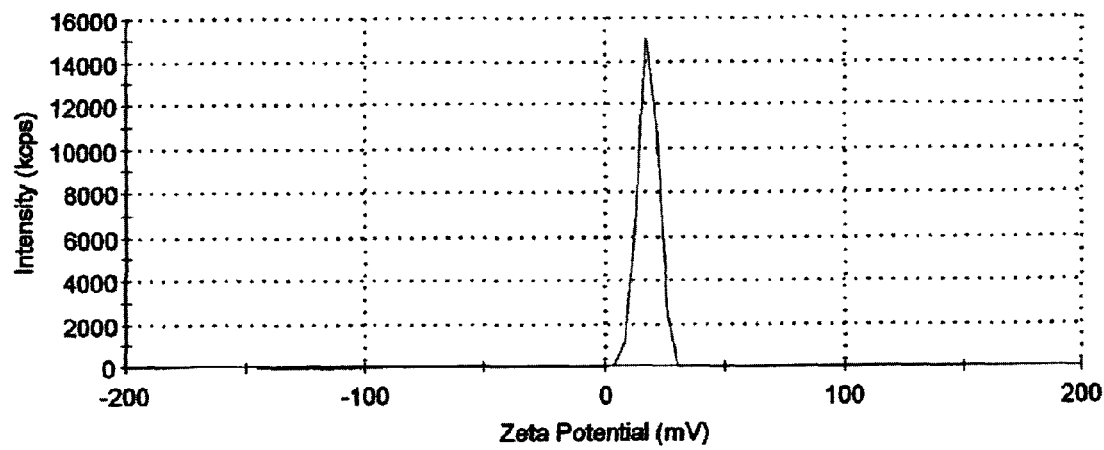
[Fig. 7]
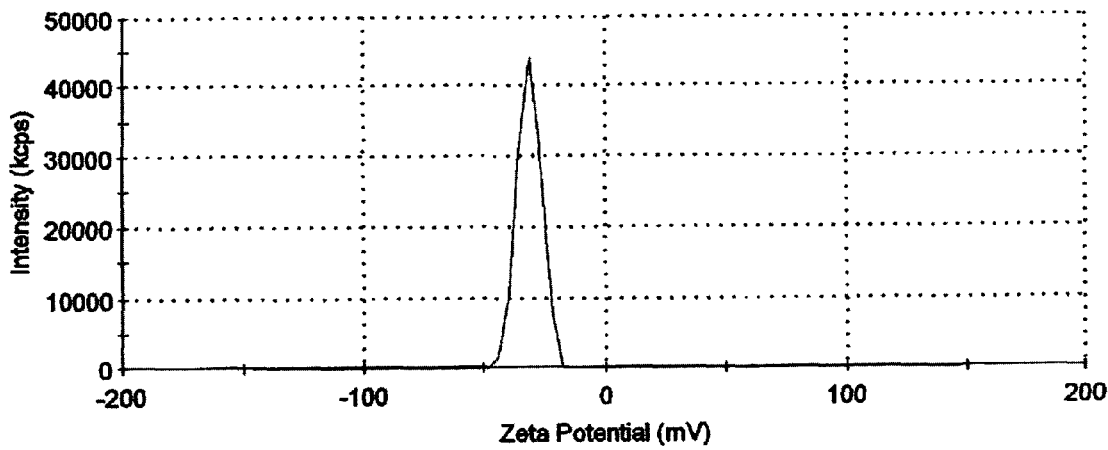

[Fig. 8]
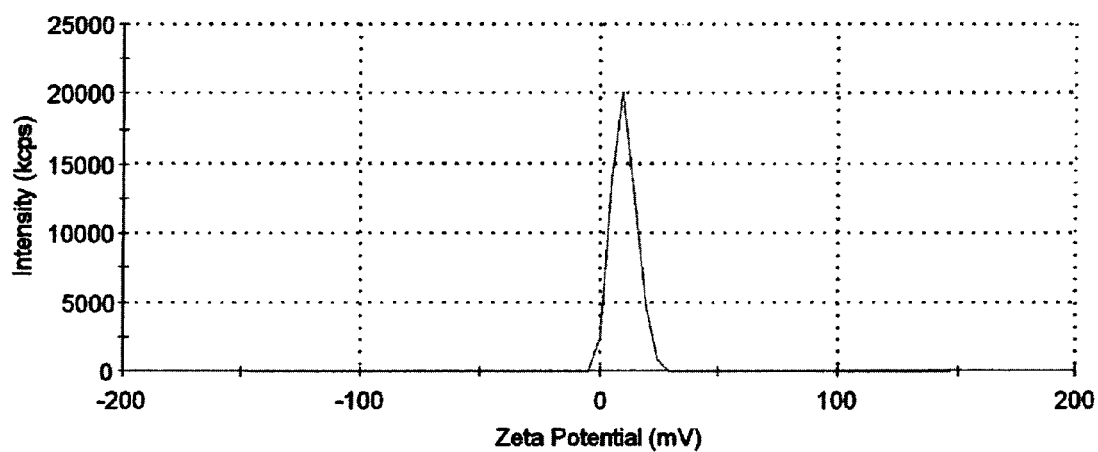
[Fig. 9]
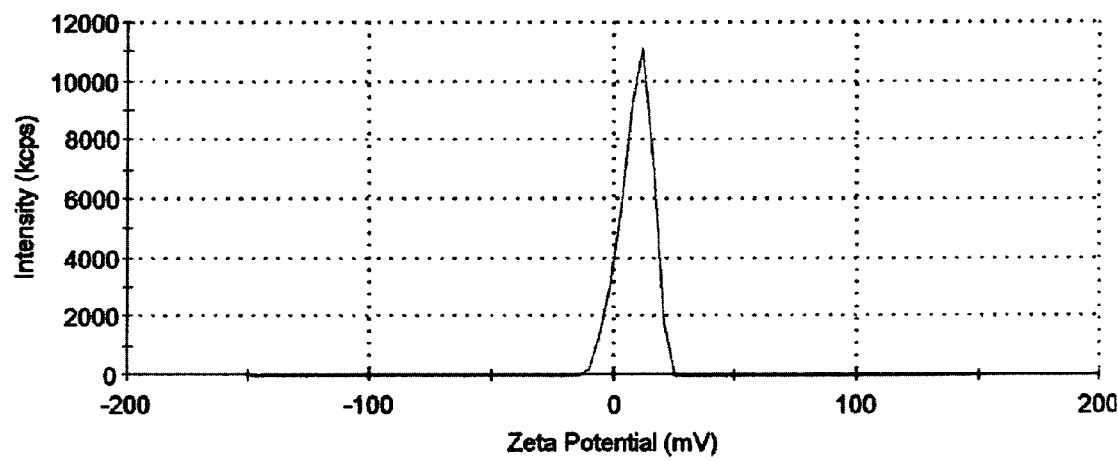

[Fig. 10]
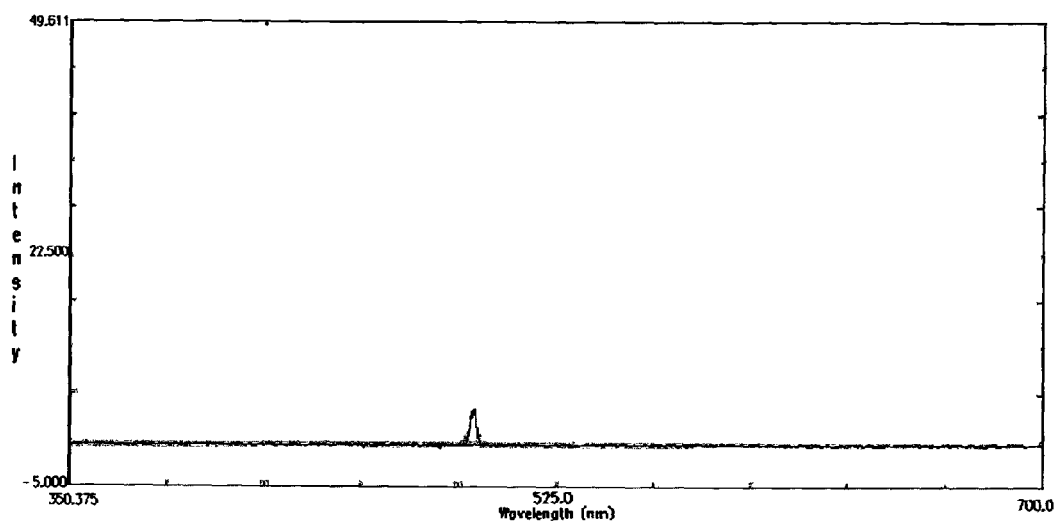
[Fig. 11]
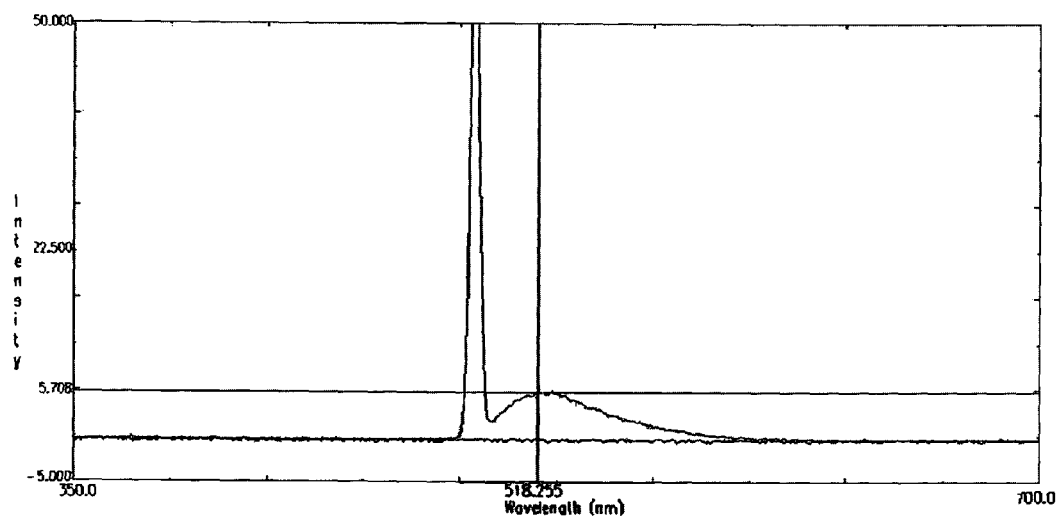

[Fig. 12]
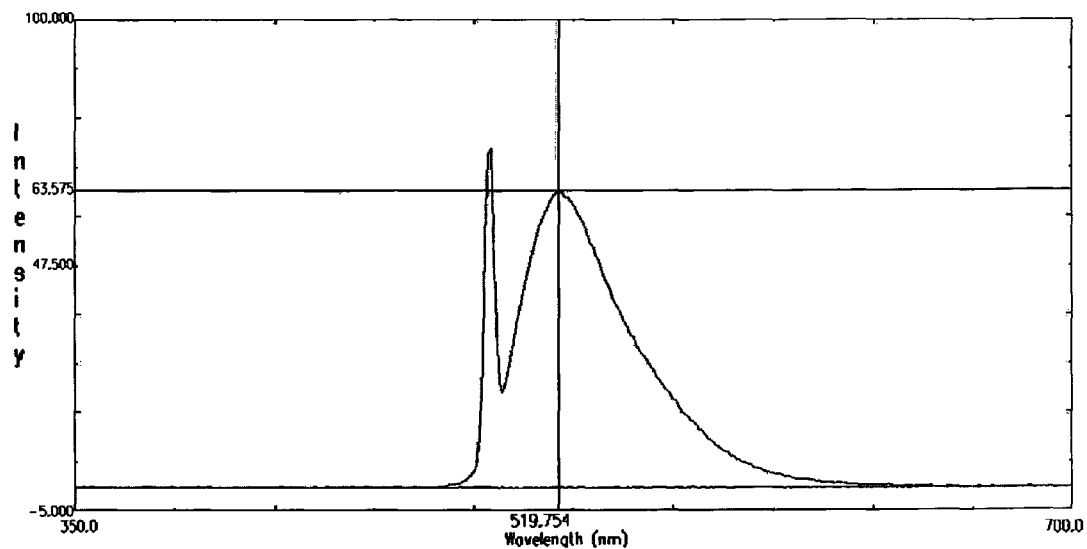
[Fig. 13]
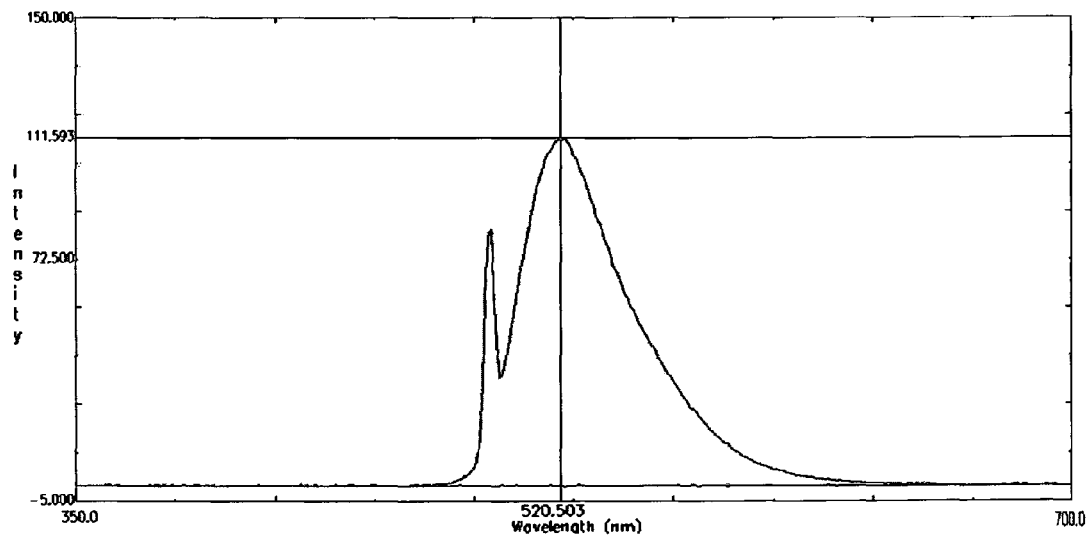

[Fig. 14]
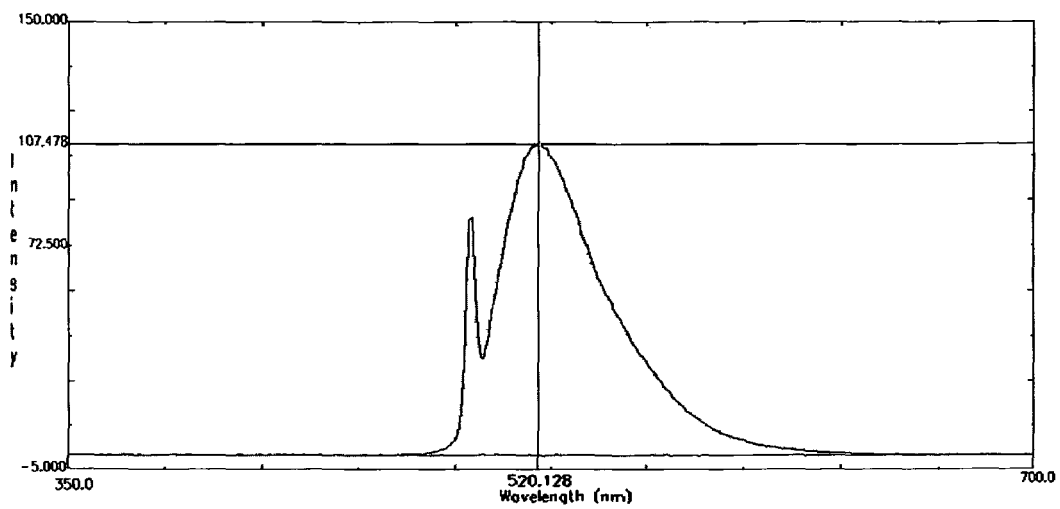
[Fig. 15]
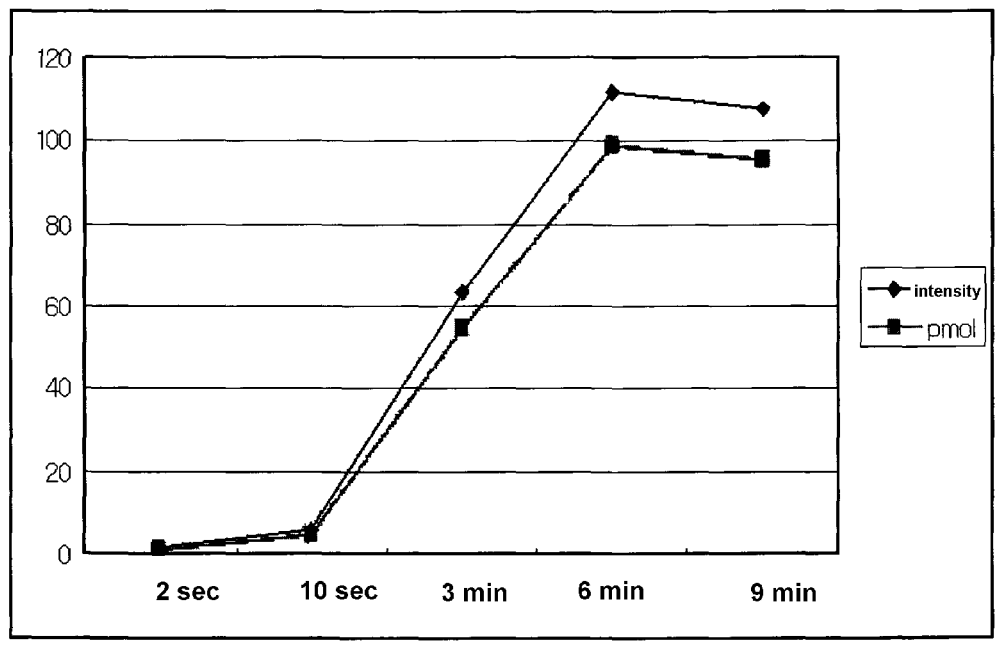

[Fig. 16]
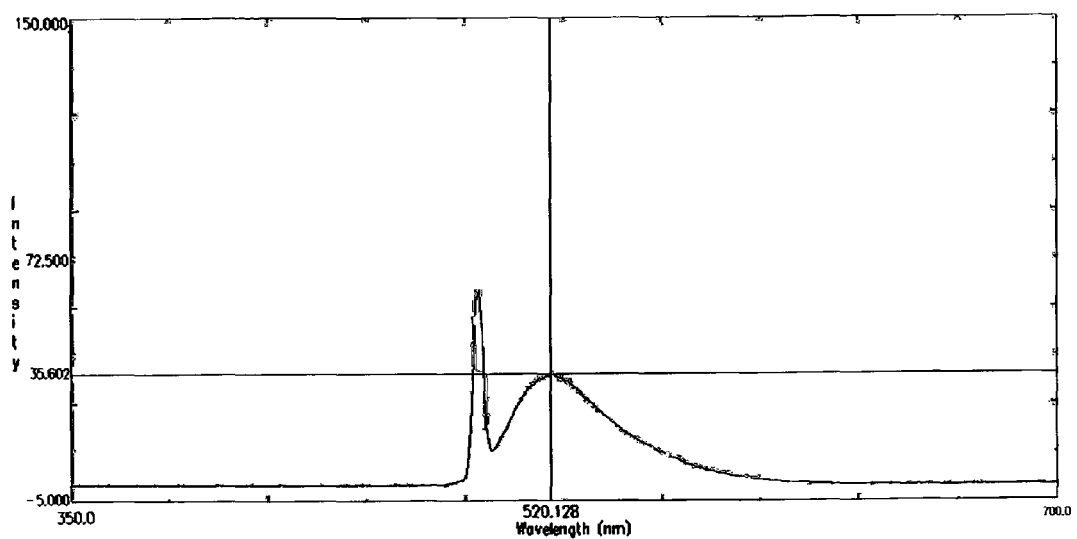
[Fig. 17]
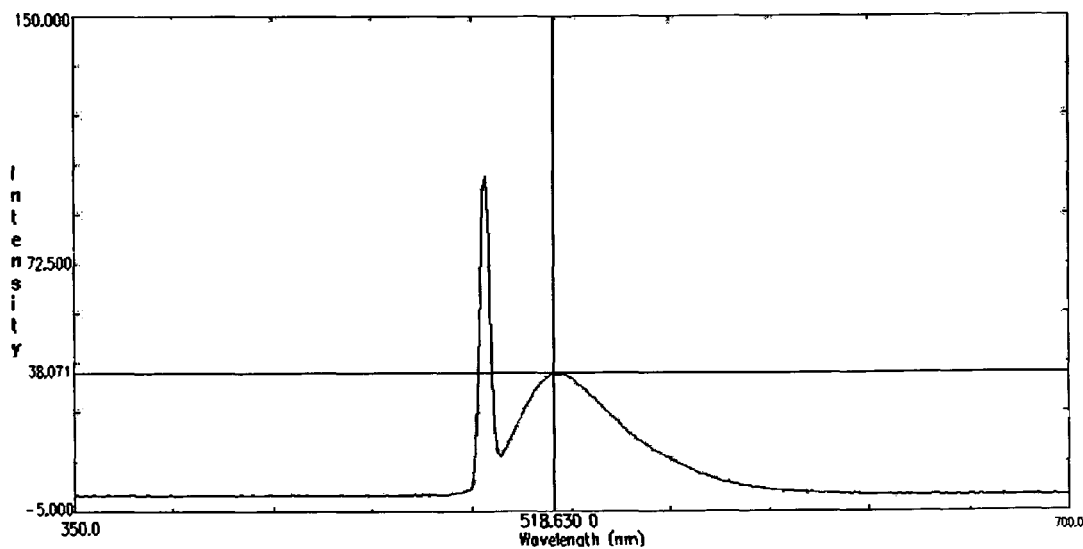

[Fig. 18]
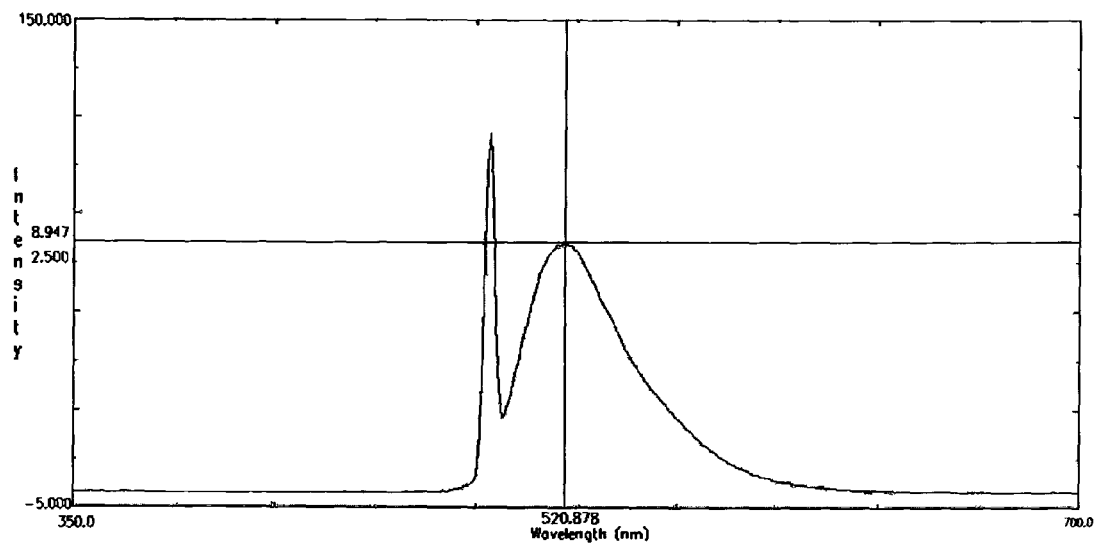
[Fig. 19]
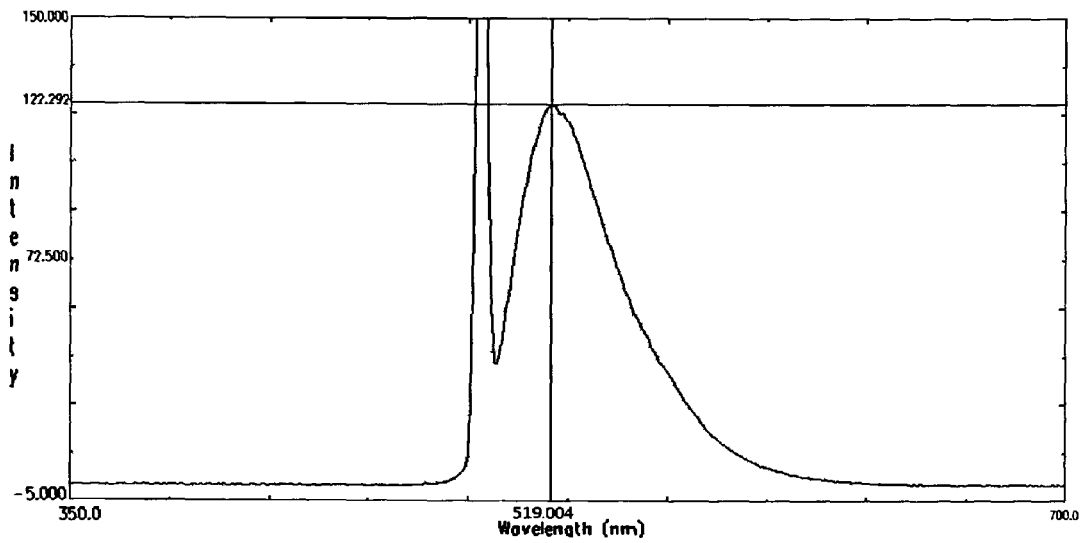

[Fig. 20]
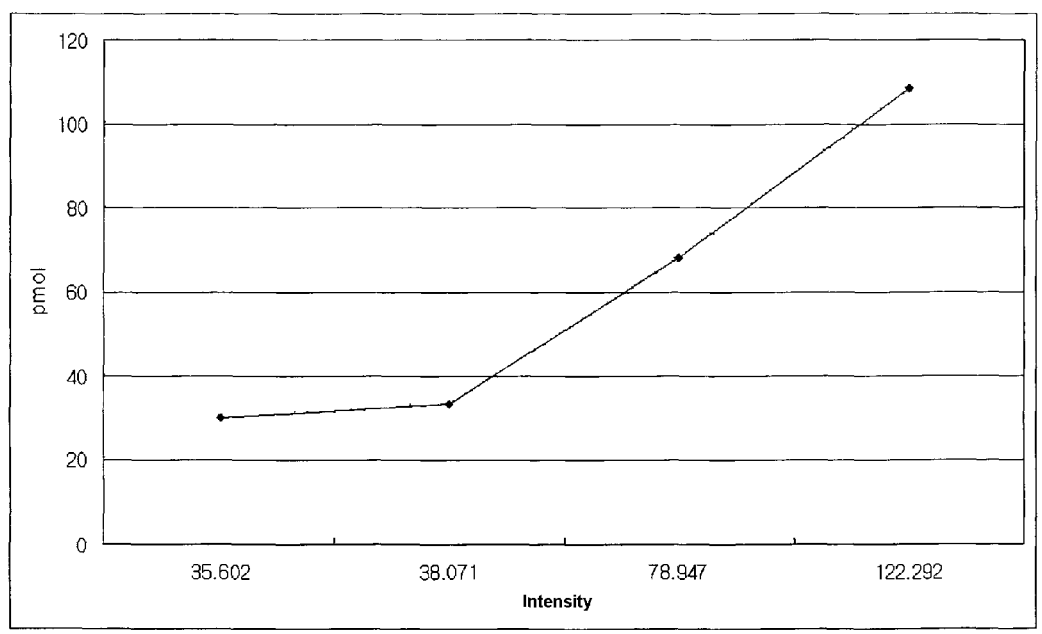

GOLD-COATED STENT, OLIGONUCLEOTIDE BOUND GOLD-COATED STENT, AND PROCESS FOR PRODUCING THE SAME

TECHNICAL FIELD

The present invention relates to a gold-plated stent and its preparation method. More specifically, it relates to a gold-plated stent that is coated with various chemical materials such as 2-aminoalkanethiol, epihalogenhydrin, and diamine compounds in a sequence and also oligonucleotide gold-plated stent, which is prepared by binding oligonucleotide, a biomaterial, to the gold-plated stent coated with said chemicals.

BACKGROUND ART

American Heart Association reported that the cardiovascular disease is the largest cause of death and more than 2,600 people die of it every day. Korea also shows the increasing prevalence rate of the disease caused by arteriosclerosis since 1980's when eating habit started to turn westernized.

Percutaneous transluminal coronary angioplasty is a method to treat stenosis when there is serious hemadostenosis after angiocardiography is conducted and it is performed for patients with stroke, angina pectoris, myocardial infarction, etc. It is an invasive treatment through blood vessels. Yet, due to the bypass, the required days for hospital treatment are shorter than those of surgeries and several follow-up operations are possible, showing low death rate. For the treatment, a guidewire is inserted into the coronary artery with lesion and a balloon catheter is put in the lesion part and then expanded by pressure to widen the narrowed lesion. The rupture, crush, and extension of atherosclerotic plaques by the expanded balloon widen the lesion. Yet, it had a disadvantage that it had to be performed several times because side effects occurred by inducing remodeling of vessels, which cause blood vessel injury, and extension of tunica media and resulting in 30~70% of patients having narrowed lesions back in six months.

Even after repeating this process several times, when there is serious stenosis or a vascular occlusion by vascular dissection and ruptured atherosclerotic plaques, then a stent, a metal mesh, is inserted to prevent it.

Since Benestent and stress clinical research in 1994, which set the ground that stent treatment can have higher restenosis reducing rate than balloon angioplasty, the stent operation has been more common up to 80~90% in coronary stenosis treatment in current clinics. Even after the stent operation became popularized, 15~20% of restenosis could not be resolved. Radioactive treatment was employed to overcome it, but its use was limited due to later restenosis and thrombosis. However, to overcome the problem, agent-coated stents were recently developed, reducing the restenosis rate on the stent surface down to less than 10% by using anticancer agents or immunosuppressants (examples of Sirolimus eluting stents are Ravel, *Sirius, C- & E- Sirius, Direct, Svelte, Sirius, Reality*; examples of Paclitaxel-eluting stents are *Taxus I~VI, Endeavor-I~III* etc.) and their efficiency was proven through the research. Yet, since these agents that coat stents use anticancer agents or immunosuppressants, there is a possibility of toxicity in endotheliocytes.

The percutaneous coronary interventions are performed over 10,000 times a year in Korea, and the domestic market is worth more than 20 million dollars. The stents for angioplasty have been barely domesticated and also all medical materials and agents developed overseas cost a huge amount of national wealth for paying royalty every year. Thus, it is expected that new targets of cardiovascular diseases and the development of new drugs will bring enormous economical and social profits. Since it was reported that the agent-coated stents deliver local agents effectively and continuously and remarkably reduce the restenosis rate within stents, they have been recently on the market in the nation at about twice higher price than the existing stents. Also, the future market of agent-coated stents is expected to grow much faster, so there is a desperate need for their technical development.

On the other hand, the biomaterial agent market is on the rise all over the world now. Among RNA researches, the RNA interference (RNAi) research is greatly in the spotlight, especially small interfering RNA (siRNA) technology, which can induce RNA interference, is getting a lot of attention. Also, siRNA causing RNA interference intercepts gene information for protein synthesis as if it were a gene switch in RNA wire that delivers gene information, so it can be applied in various ways including infectious disease treatment as well as inherited disease treatment.

The most important matter in current RNA interference technology is that there is no siRNA delivery system, so the efficient and safe delivery system that inserts siRNA into target cells is needed to well induce RNA interference effect.

DISCLOSURE OF INVENTION

Technical Subject

For the present invention, siRNA among oligonucleotides bound to gold-plated stents is a biomaterial, which minimizes the toxicity by chemicals (drugs) and helps smooth muscle cells in the intermediate layer act in a unique way and expected to bring the effect to restrain proliferation. Also, binding siRNA with gold-plated stents and inserting it raises the local concentration in injured parts and minimizes the toxicity overall the body. The technology to chemically coat stents or transform siRNA can be respectively introduced, but the technology of siRNA binding to gold-plated stents, which was conducted in the present invention, have not performed so far and it is a novel method.

The binding of SiRNA, a biomaterial, in the present invention has the advantage that it minimizes the toxicity by chemicals and helps smooth muscle cells in the intermediate layer act in a unique way to restrain proliferation, raise the local concentration in injured parts, and minimize the toxicity overall the body.

To achieve the said purposes, the present invention has an object to provide chemically coated gold-plated stents by reacting various chemical materials on the surface of gold-plated stents in a sequence and their preparation methods.

Another object of the present invention is to provide oligonucleotide gold-plated stents, which make the gold-plated stents coated with said chemical materials bind to oligonucleotide, a biomaterial, and their preparation methods.

Technical Solution

The present invention relates to a gold-plated stent and its preparation method. More specifically, it relates to a gold-plated stent that is coated with various chemical materials such as 2-aminoalkanethiol, epihalogenhydrin, and diamine compounds in a sequence and also oligonucleotide gold-plated stent, which is prepared by binding oligonucleotide, a biomaterial, to the gold-plated stent coated with said chemicals.

Hereinafter, the present invention is described in more detail.

The present invention relates to a gold-plated stent presented as Structural Formula I below.

[Structural Formula I]

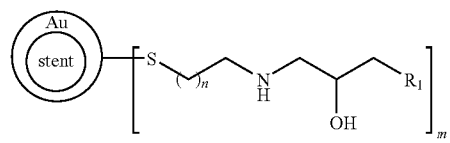

[In the above structural formula, $R_1$ is Br, Cl, or

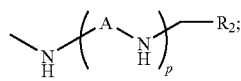

$R_2$ is hydrogen or alkyl of $C_1$-$C_{30}$ substituted with more than one selected from the amino group or alkyl amino group of $C_1$-$C_{30}$;

A is alkylene of $C_1$-$C_{30}$, and the carbon atom of the alkylene can be substituted with more than one heteroatom selected from oxygen, nitrogen, or sulfur;

m is an integer of 1 or more, n is an integer of 1 to 30, p is an integer of 1 to 30.]

In the above Structural Formula 1, m is an integer of 1 or more, surrounding the surface of the stent, so there is no significance in limiting its number.

Also, the present invention relates to a gold-plated stent bound to siRNA, which is formed by binding siRNA to the amine (—NH— or —$NH_2$) group of the stent presented as Structural Formula I. When buffer treated, the said siRNA has a (−) charge and binds to the amine (—NH— or —$NH_2$) group of the gold-plated stent that is coated with chemicals containing the amine (—NH— or —$NH_2$) group.

The gold-plated stents of the present invention include the gold-plated stent of Structural Formula I-1 below, the gold-plated stent having amine(-NH—) of Structural Formula I-2, the gold-plated stent having amine(-NH— or —$NH_2$) of Structural Formula II, and the gold-plated stent that has the amine group of the said stent binding to oligonucleotide. It is preferable that the said oligonucleotide is selected from the group consisting of DNA, RNA, and siRNA, and more preferable that it is siRNA (small interfering RNA).

The characteristic of the said oligonucleotide is that it is selected from the group consisting of DNA, RNA, and siRNA. Just as siRNA with the (−) charge when buffer treated binds to the gold-plated stents, DNA and RNA can also bind to the gold-plated stents having charges.

[Structural Formula I-1]

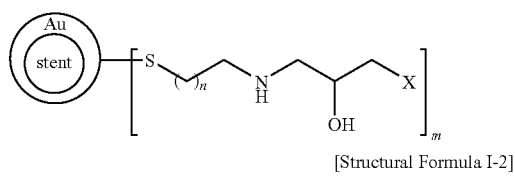

[Structural Formula I-2]

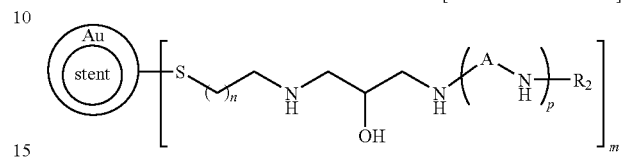

[Structural Formula II]

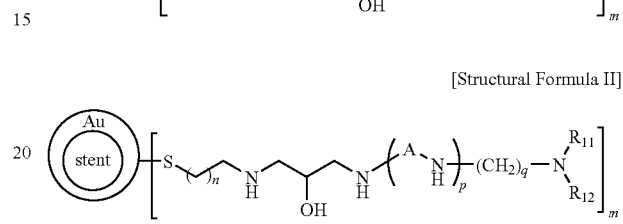

[In the above structural formulas, A, $R_2$, n, and p is the same as the above Structural Formula I; X is Br or Cl; $R_{11}$ and $R_{12}$ are independently hydrogen or alkyl of $C_1$-$C_{30}$; m is an integer of 1 to 1 million; q is an integer of 1 to 30.]

For the gold-plated stents of the present invention, it is preferable to be the gold-plated stent containing the amine group (—NH— or —$NH_2$) of the Structural Formula III below, and more preferable to be the gold-plated stent that has siRNA (small interfering RNA) binding to the amine group (—NH— or —$NH_2$) of the gold-plated stent containing the amine group (—NH— or —$NH_2$) of the Structural Formula III below. It is shown in FIG. 1.

[Structural Formula III]

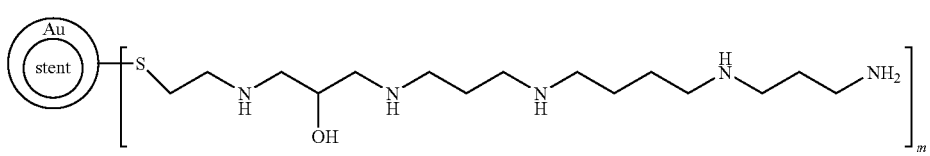

[In the above structural formula, m is an integer of 1 to 1 million.]

The gold-plated stent of the present invention presented as Structural Formula I-1 is prepared through the steps below.

1) a step where the stent in Structural Formula V below is formed by the reaction of the gold-plated stent in Structural Formula IV below with 2-aminoalkanethiol in Chemical Formula 1; and 2) a step where the stent of Structural Formula I-1 below is formed by the epoxy ring opening reaction of the stent having sulfur bonding in Structural Formula V below and epihalogenhydrin in Chemical Formula 2;

[Structural Formula IV]

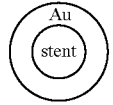

[Structural Formula V]

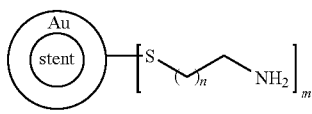

[Structural Formula I-1]

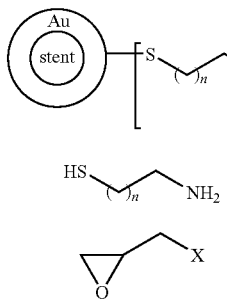

[Chemical Formula 1]

HS—(CH₂)ₙ—NH₂

[Chemical Formula 2]

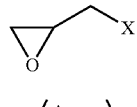

[In the above structural formulas and chemical formulas, X is Br or Cl; m is an integer of 1 or more; n is an integer of 1 to 30.]

The gold-plated stent containing the amine group (—NH— or —NH₂) of Structural Formula I-2 by the present invention is prepared through the steps below.

1) a step where the stent having sulfur bonding in Structural Formula V below is formed by the reaction of the gold-plated stent in Structural Formula IV below and 2-aminoalkanethiol in Chemical Formula 1;

2) a step where the stent of Structural Formula I-1 below is formed by the epoxy ring opening reaction of the stent having sulfur bonding in Structural Formula V below and epihalogenhydrin in Chemical Formula 2; and 3) a step where the stent containing the amine group (—NH— or —NH₂) of Structural Formula I-2 below is formed by the reaction of the prepared stent in Structural Formula I-1 below and the diamine compound in Chemical Formula 3.

[Structural Formula IV]

[Structural Formula V]

[Structural Formula I-1]

[Structural Formula I-2]

[Chemical Formula 1]

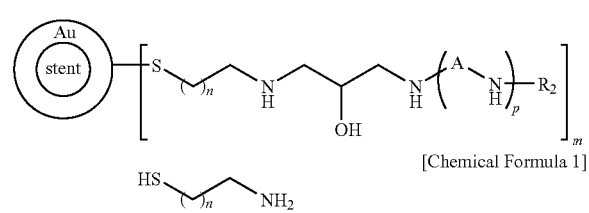

[Chemical Formula 2]

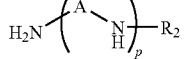

[Chemical Formula 3]

H₂N—(A—NH)ₚ—R₂

[In the above structural formulas and chemical formulas, A is alkylene of $C_1$-$C_{30}$, and the carbon atom of the alkylene can be substituted with more than one heteroatom selected from oxygen, nitrogen, or sulfur; $R_2$ is hydrogen or alkyl of $C_1$-$C_{30}$ substituted with more than one selected from the amino group or alkyl amino group of $C_1$-$C_{30}$; X is Br or Cl; m is an integer of 1 or more; n is an integer of 1 to 30; p is an integer of 1 to 30.]

The gold-plated stent having oligonucleotide of Structural Formula I-3 binding to the amine group (—NH— or —NH₂) by the present invention is prepared through the steps below.

1) a step where the stent of Structural Formula V below is formed by the reaction of the gold-plated stent in Structural Formula IV below and 2-aminoalkanethiol in Chemical Formula 1;

2) a step where the stent of Structural Formula I-1 below is formed by the reaction of the stent in Structural Formula V below and epihalogenhydrin in Chemical Formula 2;

3) a step where the stent of Structural Formula I-2 below is formed by the reaction of the prepared stent in Structural Formula I-1 below and the diamine compound in Chemical Formula 3; and 4) a step where the gold-plated stent binding to siRNA (small interfering RNA) is formed by binding the amine group (—NH— or —NH₂) of the prepared stent in Structural Formula I-2 below with oligonucleotide.

[Structural Formula IV]

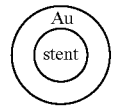

[Structural Formula V]

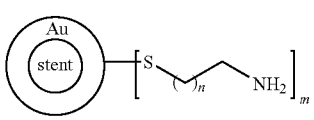

[Structural Formula I-1]

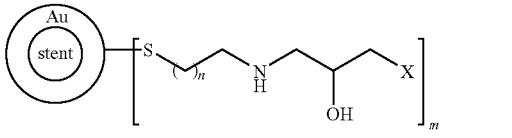

[Structural Formula I-2]

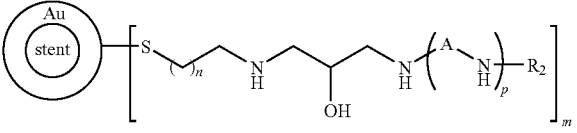

[Chemical Formula 1]

HS—(CH₂)ₙ—NH₂

[Chemical Formula 2]

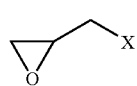

-continued

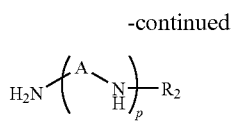

[Chemical Formula 3]

[In the above structural formulas and chemical formulas, A is alkylene of $C_1$-$C_{30}$, and the carbon atom of the alkylene can be substituted with more than one heteroatom selected from oxygen, nitrogen, or sulfur; $R_2$ is hydrogen or alkyl of $C_1$-$C_{30}$ substituted with more than one selected from the amino group or alkyl amino group of $C_1$-$C_{30}$; X is Br or Cl; m is an integer of 1 or more; n is an integer of 1 to 30; p is an integer of 1 to 30.]

The stent including amine (—NH— or —$NH_2$) of the Structural Formula I-2 contains the amine group (—NH— or —$NH_2$) within the chain, so it is possible to deliver oligonucleotide to the blood vessel through the gold-plated stent binding to oligonucleotide, which is prepared by the said amine group that binds to oligonucleotide, a biomaterial.

At 5' of siRNA oligo used as oligonucleotide in the present invention, fluorescein, which has high fluorescence, was bound to the gold-plated stent and detected by a spectrofluorophotometer.

BRIEF DESCRIPTION OF DRAWINGS

FIG. 1—one example of the siRNA gold-plated stent that has a chemically coated gold-plated stent binding to siRNA, a biomaterial.

FIG. 2—IR spectrum of Example 1 with no samples added (the control group).

FIG. 3—IR spectrum of Compound C prepared in Example 1.

FIG. 4—IR spectrum of Compound D prepared in Example 1.

FIG. 5—IR spectrum of the gold (Au) compound having the amine compound of Compound E prepared in Example 1.

FIG. 6—a graph showing the zeta-potential measurement of pure gold foil used in Example 1.

FIG. 7—a graph showing the zeta-potential measurement of Compound C prepared in Example 1.

FIG. 8—a graph showing the zeta-potential measurement of Compound D prepared in Example 1.

FIG. 9—a graph showing the zeta-potential measurement of Compound E prepared in Example 1.

FIG. 10—a spectrum measured by the spectrofluorophotometer using the sodium carbonate buffer (pH 11) in Example 2 (the control group).

FIG. 11—a spectrum showing 5'-fluorescein measured by the spectrofluorophotometer after siRNA bound gold-plated stent is reacted for 10 seconds under the sodium carbonate buffer in Example 2.

FIG. 12—a spectrum showing 5'-fluorescein measured by the spectrofluorophotometer after siRNA bound gold-plated stent is reacted for 3 minutes under the sodium carbonate buffer in Example 2.

FIG. 13—a spectrum showing 5'-fluorescein measured by the spectrofluorophotometer after siRNA bound gold-plated stent is reacted for 6 minutes under the sodium carbonate buffer in Example 2.

FIG. 14—a spectrum showing 5'-fluorescein measured by the spectrofluorophotometer after siRNA bound gold-plated stent is reacted for 9 minutes under the sodium carbonate buffer in Example 2.

FIG. 15—a graph showing the measured amount of the binding of gold-plated stent and siRNA using 5'-fluorescein siRNA in Example 2.

FIG. 16—a spectrum showing 5'-fluorescein measured by the spectrofluorophotometer after quantifying 30 pmol of 5'-fluorescein siRNA oligo under the sodium carbonate buffer in Example 2.

FIG. 17—a spectrum showing 5'-fluorescein measured by the spectrofluorophotometer after quantifying 33.2 pmol of 5'-fluorescein siRNA oligo under the sodium carbonate buffer in Example 2.

FIG. 18—a spectrum showing 5'-fluorescein measured by the spectrofluorophotometer after quantifying 68 pmol of 5'-fluorescein siRNA oligo under the sodium carbonate buffer in Example 2.

FIG. 19—a spectrum showing 5'-fluorescein measured by the spectrofluorophotometer after quantifying 108.5 pmol of 5'-fluorescein siRNA oligo under the sodium carbonate buffer in Example 2.

FIG. 20—a graph showing backward quantification of the binding state of the stent and siRNA in highest concentration using 5'-fluorescein siRNA in Example 2.

BEST MODE

The present invention is described in more detail based on the examples below, but the examples are only to help the understanding and do not restrict the range of the present invention.

Example 1

Preparation of Gold-Plated Stents Coated with Chemicals (Structural Formula III)

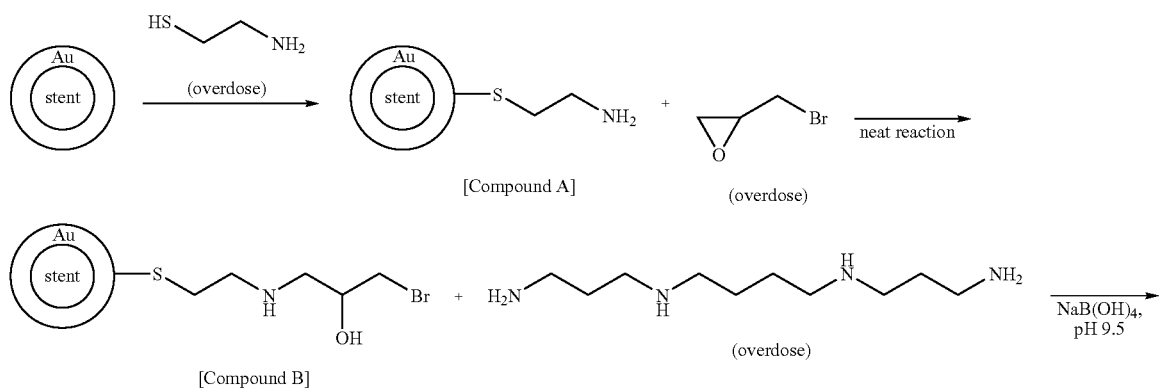

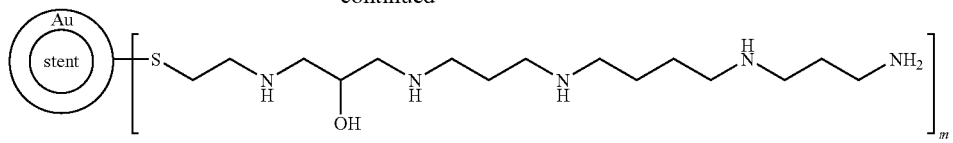

[Formula III]

[In the above formula, m is an integer of 1 to 1 million.]

Under ethanol, the gold-plated stent (0.0165 g, 0.084 mmol) [gold-plated stent=0.03 μm thickness of thin film, Daeduck Chemical] and the overdose of 2-aminoethanethiol (3.88 mmol, 46 times amount of gold-plated stent, Aldrich) was used and sonicated for 2 hours at room temperature to synthesize the gold-plated stent that had sulfur bonding on the surface [Compound A]. The said stent [Compound A] was washed three times by 20 ml of acetonitrile and another stent [Compound B] was synthesized by neat reaction of triethylamine (3.36 mmol, 40 times amount of gold-plated stent) and overdose of epibromohydrin (3.53 mmol, 42 times amount of gold-plated stent, Aldrich).

Using spermine (2.52 mmol, 30 times amount of gold-plated stent) purchased from Aldrich, the synthesized stent [Compound B] was reacted in the sodium boric acid buffer (pH 9.5) and washed three times by acetonitrile to obtain the stent containing amine (—NH— or $NH_2$) [Structural Formula III].

IR and zeta-potential were measured to check if the chemicals, which are used to prepared stent containing amine (—NH— or $NH_2$) presented as Structural Formula III, bond in a sequence. Since stents are metal meshes, it is not possible to measure NMR, IR, mp, etc. Thus, gold foil (DongYang Gold Silver Leaf & Powder Ind., Co.) was employed instead of gold-plated stents of the present invention and reacted in a sequence with 2-aminoethanethiol, epibromohydrin, and spermine to respectively synthesize Compound C, Compound D, and Compound E. The IR and zeta-potential of those amine terminated compounds were measured. FIGS. 2 to 9 show the result.

FIGS. 2 and 6 are the control groups. FIGS. 3 to 5 show the IR of the amine terminated compounds of Compound C, D, and E. FIGS. 7 to 9 show the result of zeta-potential of the amine terminated compounds of Compound C, D, and E.

When compared with the control group of FIG. 2, it was found that there was the amine group in the range of 3300 $cm^{-1}$~3500 $cm^{-1}$, $CH_2$—Br bending in 1250 $cm^{-1}$~1190 $cm^{-1}$, and the C—O stretch of primary alcohol in 1050 $cm^{-1}$ from the IR spectrum of FIGS. 3 to 5.

Also, when compared with FIG. 5 (the control group) having (+) charge in pure gold, the synthesis could be found out by the change in charge value of zeta-potential in FIGS. 7 to 9. Gold has +2 value, so it has a (+) charge by itself, and when amine (N+) is combined at the terminus, (−) values are gathered around it, which changes zeta-potential to (−), so whether it is synthesized or not can be decided by the change of charge.

Example 2

Preparation of the Gold-Plated Stent Binding to siRNA (Small Interfering RNA)

10 nmol of 5'-fluorescein siRNA oligo (CCU ACG CCA CCA AUU UCG U; sequence listing 1) was diluted by 1000 μl of the Tris buffer (Bioneer Corp. pH 7.4). Then, the stent containing the amine group prepared in Example 1 [Structural Formula III] was added for reaction for 5 minutes and washed five times by 1ml of DEPC DW(Diethyl pyrocarbonate treated distilled water, Bioneer) to obtain the gold-plated stent wherein siRNA is bound to the amine group. FIG. 1 shows some part of it.

[Structural Formula III]

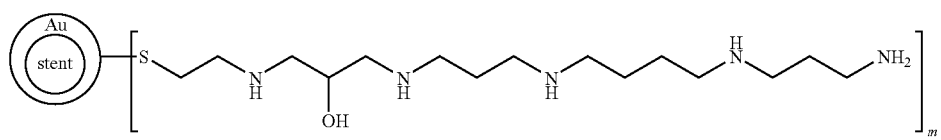

[In the structural formula above, m is an integer of 1 to 1 million.]

The gold-plated stent wherein siRNA (small interfering RNA) was bound to amine (—NH— or —$NH_2$) was put at regular intervals in 3 ml of the buffer (pH 11) prepared by using sodium carbonate ($Na_2CO_3$, Aldrich). The fluorescein (showing fluorescence at 5' of siRNA oligo) that had fell off was measured by spectrofluorophotometer (SHIMADZU, RF-5301PC). Table 1 below and FIGS. 9 to 14 show it and it was found that it had highest intensity of 107.478 when 9 minutes passed.

TABLE 1

| | Reaction Time | | | | |
|---|---|---|---|---|---|
| | 2 seconds | 10 seconds | 3 minutes | 6 minutes | 9 minutes |
| Intensity | 1.619 | 5.708 | 63.575 | 111.593 | 107.478 |
| pmol | 1.355 | 4.810 | 54.759 | 99.244 | 95.584 |

In Table 1, to backward quantify the amount of fluorescein when 9 minutes passed and showed the highest intensity, 107.478, the gold-plated stent wherein siRNA is bound to amine (—NHx) [Structural Formula III] was put at regular intervals in 3 ml of the buffer (pH 11) prepared by using sodium carbonate ($Na_2CO_3$, Aldrich). The fluorescein (showing fluorescence at 5' of siRNA oligo) that had fell off was measured by spectrofluorophotometer (SHIMADZU, RF-5301PC) and its amount was backward quantified. Table 2 below and FIGS. 15 to 19 show the intensity and pmol and it was found that the intensity of 107.478 was approximately 100 pmol.

TABLE 2

| Intensity | 35.602 | 38.071 | 78.947 | 122.292 |
|---|---|---|---|---|
| pmol | 30 | 33.2 | 68 | 108.5 |

INDUSTRIAL APPLICABILITY

As presented above, it was found that siRNA was bound to the gold-plated stent compound after measuring fluorescein

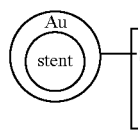

at 5' of siRNA oligo, oligonucleotide, on the surface of the stent by the spectrofluorophotometer.

Also, the various existing anticancer agents used for coating stents showed toxicity in endotheliocytes, but the gold-plated stent of the present invention has oligonucleotide binding, which is a biomaterial, and is expected to minimize the toxicity by chemicals and help smooth muscle cells in the intermediate layer act in a unique way to restrain proliferation, raise the local concentration in injured parts, and minimize the toxicity overall the body.

The invention claimed is:

1. A gold-plated stent presented as Structural Formula I below,

[Structural Formula I]

in the above structural formula, $R_1$ is Br, Cl, or

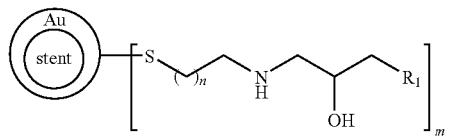

$R_2$ is hydrogen or alkyl of $C_1$-$C_{30}$ substituted with more than one group selected from an amino group or alkyl amino group of $C_1$-$C_{30}$;

A is alkylene of $C_1$-$C_{30}$, which can be substituted with more than one heteroatom selected from oxygen, nitrogen, or sulfur; and m is an integer of 1 or more, n is an integer of 1 to 30, p is an integer of 1 to 30.

2. The gold-plated stent of claim 1, wherein said stent is presented as Structural Formula II below,

[Structural Formula II]

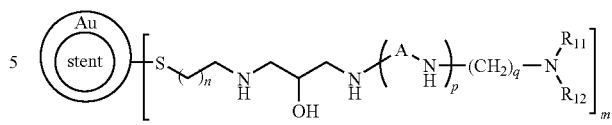

in the above structural formulas, m is an integer of 1 to 1 million; $R_{11}$ and $R_{12}$ are independently hydrogen or alkyl of $C_1$-$C_{30}$; q is an integer of 1 to 30.

3. The gold-plated stent of claim 2, wherein said stent is presented as Structural Formula III below,

[Structural Formula III]

in the above structural formula, m is an integer of 1 to 1 million.

4. The gold-plated stent formed by binding oligonucleotide to amino group in the gold-plated stent of claim 1.

5. The gold-plated stent of claim 4, wherein said oligonucleotide is selected from the group consisting of DNA, RNA and siRNA.

6. A preparation method of gold-plated stent of Structural Formula I-2 comprising the steps of:

1) reacting a gold-plated stent in Structural Formula IV, which is

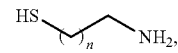

With 2-aminoalkanethiol in Chemical Formula 1, which is

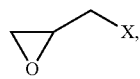

to form a stent of Structural Formula V, which is

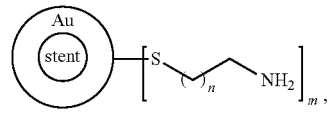

2) reacting Structural Formula V with epihalogenhydrin in Chemical Formula 2, which is to form a stent of Structural Formula I-1, which is

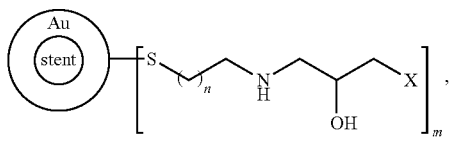

and
3) reacting Structural Formula I-1 with a diamine compound in Chemical Formula 3, which is

to form the stent of Structural Formula I-2, which is

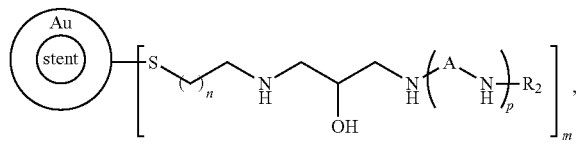

wherein
in the above structural formulas and chemical formulas, A is alkylene of $C_1$-$C_{30}$, which can be substituted with more than one heteroatom selected from oxygen, nitrogen, or sulfur;
$R_2$ is hydrogen or alkyl of $C_1$-$C_{30}$ substituted with more than one group selected from an amino group or alkyl amino group of $C_1$-$C_{30}$;
X is Br or Cl; and
m is an integer of 1 or more; n is an integer of 1 to 30; p is an integer of 1 to 30.

7. A preparation method of gold-plated stent comprising the steps of:
1) reacting a gold-plated stent in Structural Formula IV, which is

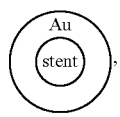

with 2-aminoalkanethiol in Chemical Formula 1, which is

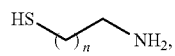

to form a stent of Structural Formula V, which is

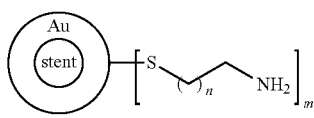

2) reacting the Structural Formula V with epihalogenhydrin in Chemical Formula 2, which is

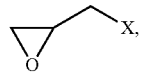

to form a stent of Structural Formula I-1, which is

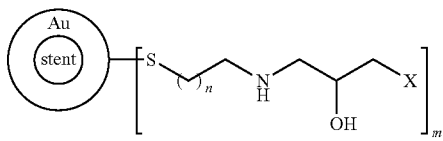

3) reacting the Structural Formula I-1 with a diamine compound in Chemical Formula 3, which is

to form a stent of Structural Formula I-2, which is

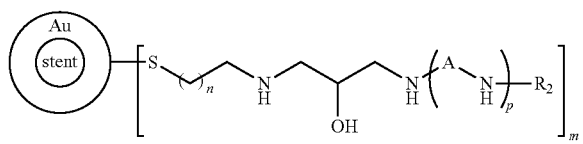

and
4) binding an amine group (—NH— or —$NH_2$) of the prepared stent in Structural Formula I-2 with oligonucleotide to form the gold-plated stent, wherein amine group (NH or $NH_2$)
in the above structural formulas and chemical formulas, A is alkylene of $C_1$-$C_{30}$, which can be substituted with more than one heteroatom selected from oxygen, nitrogen, or sulfur;
$R_2$ is hydrogen or alkyl of $C_1$-$C_{30}$ substituted with more than one group selected from the amino group or alkyl amino group of $C_1$-$C_{30}$;
X is Br or Cl; and
m is an integer of 1 or more; n is an integer of 1 to 30; p is an integer of 1 to 30.

8. A preparation method of gold-plated stent of Structural Formula I-1 comprising the steps of:
1) reacting a gold-plated stent in Structural Formula IV, which is

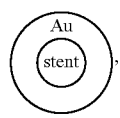

with 2-aminoalkanethiol in Chemical Formula 1, which is

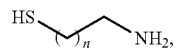

to form a stent of Structural Formula V, which is

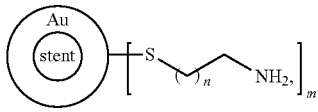

and 2) reacting the Structural Formula V with epihalogenhydrin in Chemical Formula 2, which is

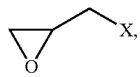

to form the stent of Structural Formula I-1, which is

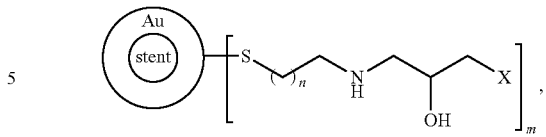

wherein;
in the above structural formulas and chemical formulas, X is Br or Cl; m is an integer of 1 or more; n is an integer of 1 to 30.

9. The gold-plated stent formed by binding oligonucleotide to amino group in the gold-plated stent of claim 2.

10. The gold-plated stent formed by binding oligonucleotide to amino group in the gold-plated stent of claim 3.

* * * * *